(12) United States Patent
Yanagisawa

(10) Patent No.: US 11,369,252 B2
(45) Date of Patent: Jun. 28, 2022

(54) ENDOSCOPE SYSTEM, CONTROL DEVICE, CONTROL METHOD, AND COMPUTER-READABLE RECORDING MEDIUM

(71) Applicant: OLYMPUS CORPORATION, Tokyo (JP)

(72) Inventor: Teppei Yanagisawa, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 71 days.

(21) Appl. No.: 16/849,385

(22) Filed: Apr. 15, 2020

(65) Prior Publication Data

US 2020/0237183 A1 Jul. 30, 2020

Related U.S. Application Data

(63) Continuation of application No. PCT/JP2018/030690, filed on Aug. 20, 2018.

(30) Foreign Application Priority Data

Dec. 21, 2017 (JP) .............................. JP2017-244756

(51) Int. Cl.
*A61B 1/00* (2006.01)
*A61B 1/04* (2006.01)
*G02B 23/24* (2006.01)

(52) U.S. Cl.
CPC ...... *A61B 1/00006* (2013.01); *A61B 1/00018* (2013.01); *A61B 1/00096* (2013.01);
(Continued)

(58) Field of Classification Search
CPC ............ A61B 1/00006; A61B 1/00018; A61B 1/00096; A61B 1/00114; A61B 1/00133;
(Continued)

(56) References Cited

U.S. PATENT DOCUMENTS

2009/0185032 A1 7/2009 Sakai et al.
2012/0162402 A1* 6/2012 Amano .............. A61B 1/00188
348/65
(Continued)

FOREIGN PATENT DOCUMENTS

JP 2010-020104 A 1/2010
JP 2011-146772 A 7/2011
(Continued)

OTHER PUBLICATIONS

International Search Report dated Sep. 11, 2018 issued in PCT/JP2018/030690.

*Primary Examiner* — Timothy J Neal
*Assistant Examiner* — Sung Ham
(74) *Attorney, Agent, or Firm* — Scully, Scott, Murphy & Presser, P.C.

(57) ABSTRACT

An endoscope system having: a transmission cable electrically connecting an actuator that moves an optical element along an optical axis direction and a driving signal generator for generating and supplying a driving signal for driving the actuator; a detector configured to detect magnitude of the driving signal output from the driving signal generator to be supplied to the actuator through the transmission cable; and a processor configured to supply the driving signal with an initial driving voltage value to the actuator for a predetermined time, calculate a combined resistance value including a resistance value of the transmission cable and a resistance value of the actuator, based on at least the detected magnitude of the driving signal, calculate a driving voltage of the actuator, based on the calculated combined resistance value and a preset rated current value of the actuator, and cause a storage to record the calculated driving voltage.

14 Claims, 11 Drawing Sheets

(52) U.S. Cl.
CPC ...... *A61B 1/00114* (2013.01); *A61B 1/00133* (2013.01); *A61B 1/04* (2013.01); *G02B 23/2407* (2013.01)

(58) Field of Classification Search
CPC ....... A61B 1/04; A61B 1/00057; A61B 1/045; A61B 1/00188; A61B 1/05; G02B 23/2407; G02B 7/09; G02B 7/102; G02B 7/105; G02B 23/2438; G02B 23/26; G02B 23/243; G02B 7/04; G02B 23/2476; G02B 7/08; G02B 23/2484; H02K 33/00; H02K 41/02; H01F 7/06; H01F 7/066; H01F 7/081
USPC .................................................. 600/109, 118
See application file for complete search history.

(56) References Cited

U.S. PATENT DOCUMENTS

| | | | | |
|---|---|---|---|---|
| 2015/0138328 | A1* | 5/2015 | Yokohama | H04N 5/372 348/65 |
| 2016/0022117 | A1* | 1/2016 | Akahane | A61B 1/00009 348/65 |
| 2016/0331211 | A1* | 11/2016 | Fujisawa | A61B 1/00006 |
| 2016/0377855 | A1* | 12/2016 | Takata | A61B 1/00096 359/696 |

FOREIGN PATENT DOCUMENTS

| | | |
|---|---|---|
| JP | 2013-128663 A | 7/2013 |
| JP | 5873218 B2 | 3/2016 |
| WO | WO 2015/093398 A1 | 6/2015 |

\* cited by examiner

ENDOSCOPE SYSTEM, CONTROL DEVICE, CONTROL METHOD, AND COMPUTER-READABLE RECORDING MEDIUM

CROSS-REFERENCE TO RELATED APPLICATION

This application is a continuation of PCT International Application No. PCT/JP2018/030690 filed on Aug. 20, 2018, which designates the United States, incorporated herein by reference, and which claims the benefit of priority from Japanese Patent Application No. 2017-244756, filed on Dec. 21, 2017, incorporated herein by reference.

BACKGROUND

1. Technical Field

The present disclosure relates to an endoscope system that is to be inserted into a subject to generate image data of the subject and also relates to a control device, a control method, and a computer-readable recording medium.

2. Related Art

In the related art, a technique capable of changing a focal length of an optical system provided at a distal end portion in an endoscope has been known (see Japanese Patent No. 5873218). This technique is known to change the focal length of the optical system by changing the electric power supplied to an actuator that drives a movable lens frame that holds a movable lens provided at the distal end portion of an insertion portion so that the movable lens frame can move forward and backward in an optical axis direction. With this technique, first electric power is output to the actuator when the movable lens frame is held at a first holding position, while second electric power that is larger than the first power is output ween the movable lens frame is held at a second holding position, thereby changing the focal length of the optical system.

SUMMARY

In some embodiments, an endoscope system includes: an optical system configured to form a subject image; an actuator configured to move at least one optical element of the optical system along an optical axis direction; a driving signal generator configured to generate and supply a driving signal for driving the actuator; a transmission cable electrically connecting the actuator and the driving signal generator, the transmission cable being configured to transmit the driving signal; a detector configured to detect magnitude of the driving signal through the transmission cable; and a processor including hardware, the processor being configured to supply the driving signal with an initial driving voltage value to the actuator for a predetermined time, calculate a combined resistance value including a resistance value of the transmission cable and a resistance value of the actuator, based on at least the detected magnitude of the driving signal, calculate a driving voltage of the actuator, based on the calculated combined resistance value and a preset rated current value of the actuator, and cause a storage to record the calculated driving voltage.

In some embodiments, an endoscope system includes: an optical system configured to form a subject image; an actuator configured to move at least one optical element of the optical system along an optical axis direction; a driving signal generator configured to generate and supply a driving signal for driving the actuator; a transmission cable electrically connecting the actuator and the driving signal generator, the transmission cable being configured to transmit the driving signal; and a detector configured to detect magnitude of the driving signal through the transmission cable; a processor including hardware, the processor being configured to supply the driving signal to the actuator while changing a voltage value from an initial driving voltage value; determine whether a difference between the detected magnitude of the driving signal and a preset rated current value of the actuator is equal to or smaller than a predetermined value, and cause a storage to record the latest driving voltage of the driving signal supplied by the driving signal generator when it is determined that the difference is equal to or smaller than the predetermined value.

In some embodiments, provided is a control device being connectable with an endoscope that includes: an optical system configured to form a subject image; and an actuator configured to move at least one optical element of the optical system along an optical axis direction. The control device includes: a driving signal generator configured to generate and supply a driving signal for driving the actuator; a transmission cable electrically connecting the actuator and the driving signal generator, the transmission cable being configured to transmit the driving signal; a detector configured to detect magnitude of the driving signal through the transmission cable; and a processor including hardware, the processor being configured to supply the driving signal with an initial driving voltage value to the actuator for a predetermined time, calculate a combined resistance value including a resistance value of the transmission cable and a resistance value of the actuator, based on at least the detected magnitude of the driving signal, calculate a driving voltage of the actuator, based on the calculated combined resistance value and a preset rated current value of the actuator, and cause a storage to record the calculated driving voltage.

In some embodiments, provided is a control device being connectable with an endoscope that includes: an optical system configured to form a subject image; an actuator configured to move at least one optical element of the optical system along an optical axis direction. The control device includes: a driving signal generator configured to generate and supply a driving signal for driving the actuator; a transmission cable electrically connecting the actuator and the driving signal generator, the transmission cable being configured to transmit the driving signal; a detector configured to detect magnitude of the driving signal through the transmission cable; and a processor including hardware, the processor being configured to supply the driving signal to the actuator while changing a voltage value from an initial driving voltage value, determine whether a difference between the detected magnitude of the driving signal and a preset rated current value of the actuator is equal to or smaller than a predetermined value, and cause a storage to record the latest driving voltage of the driving signal supplied by the driving signal generator when it is determined that the difference is equal to or smaller than the predetermined value.

In some embodiments, provided is a control method executed by an endoscope system that includes: an optical system configured to form a subject image; an actuator configured to move at least one optical element of the optical system along an optical axis direction; a driving signal generator configured to generate and supply a driving signal for driving the actuator; and a transmission cable electrically connecting the actuator and the driving signal generator, the transmission cable being configured to transmit the driving signal. The control method includes: detecting magnitude of the driving signal through the transmission cable; supplying the driving signal with an initial driving voltage value to the actuator for a predetermined time; calculating a combined resistance value including a resistance value of the transmission cable and a resistance value of the actuator, based on at least the detected magnitude of the driving signal; calculating driving voltage of the actuator, based on the calculated combined resistance value and a preset rated current value of the actuator; and causing a storage to record the calculated driving voltage.

In some embodiments, provided is a control method executed by an endoscope system that includes: an optical system configured to form a subject image; an actuator configured to move at least one optical element of the optical system along an optical axis direction; a driving signal generator configured to generate and supply a driving signal for driving the actuator; and a transmission cable electrically connecting the actuator and the driving signal generator, the transmission cable being configured to transmit the driving signal. The control method includes: detecting magnitude of the driving signal through the transmission cable; supplying the driving signal to the actuator while changing a voltage value from an initial driving voltage value; determining whether a difference between the detected magnitude of the driving signal and a preset rated current value of the actuator is equal to or smaller than a predetermined value; and causing a storage to record the latest driving voltage of the driving signal supplied by the driving signal generator when it is determined that the difference is equal to or smaller than the predetermined value.

In some embodiments, provided is a non-transitory computer-readable recording medium storing an endoscope image processing program to be executed by a computer. The program causes an endoscope system that includes: an optical system configured to form a subject image; an actuator configured to move at least one optical element of the optical system along an optical axis direction; a driving signal generator configured to generate and supply a driving signal for driving the actuator; and a transmission cable electrically connecting the actuator and the driving signal generator, the transmission cable being configured to transmit the driving signal, to execute: detecting magnitude of the driving signal through the transmission cable; supplying the driving signal with an initial driving voltage value to the actuator for a predetermined time; calculating a combined resistance value including a resistance value of the transmission cable and a resistance value of the actuator, based on at least the detected magnitude of the driving signal; calculating driving voltage of the actuator, based on the calculated combined resistance value and a preset rated current value of the actuator; and causing a storage to record the calculated driving voltage.

In some embodiments, provided is a non-transitory computer-readable recording medium storing an endoscope image processing program to be executed by a computer. The program causes an endoscope system that includes: an optical system configured to form a subject image; an actuator configured to move at least one optical element of the optical system along an optical axis direction; a driving signal generator configured to generate and supply a driving signal for driving the actuator; and a transmission cable electrically connecting the actuator and the driving signal generator, the transmission cable being configured to transmit the driving signal, to execute: detecting magnitude of the driving signal through the transmission cable; supplying the driving signal to the actuator while changing a voltage value from an initial driving voltage value; determining whether a difference between the detected magnitude of the driving signal and a preset rated current value of the actuator is equal to or smaller than a predetermined value; and causing a storage to record the latest driving voltage of the driving signal supplied by the driving signal generator when it is determined that the difference is equal to or smaller than the predetermined value.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, embodiments for carrying out the disclosure will be described in detail with reference to the drawings. Note that the disclosure is not limited to the following embodiments. Furthermore, the drawings referred to in the following description are illustrated with schematic shape, size, and positional relationship only sufficient for understanding the content of the disclosure. Thus, the disclosure is not limited only to the shape, size, and positional relationship illustrated in each drawing. Furthermore, in the following description, an endoscope system including a flexible endoscope will be described as an example of the endoscope system.

First Embodiment

Configuration of Endoscope System

Figure 1:
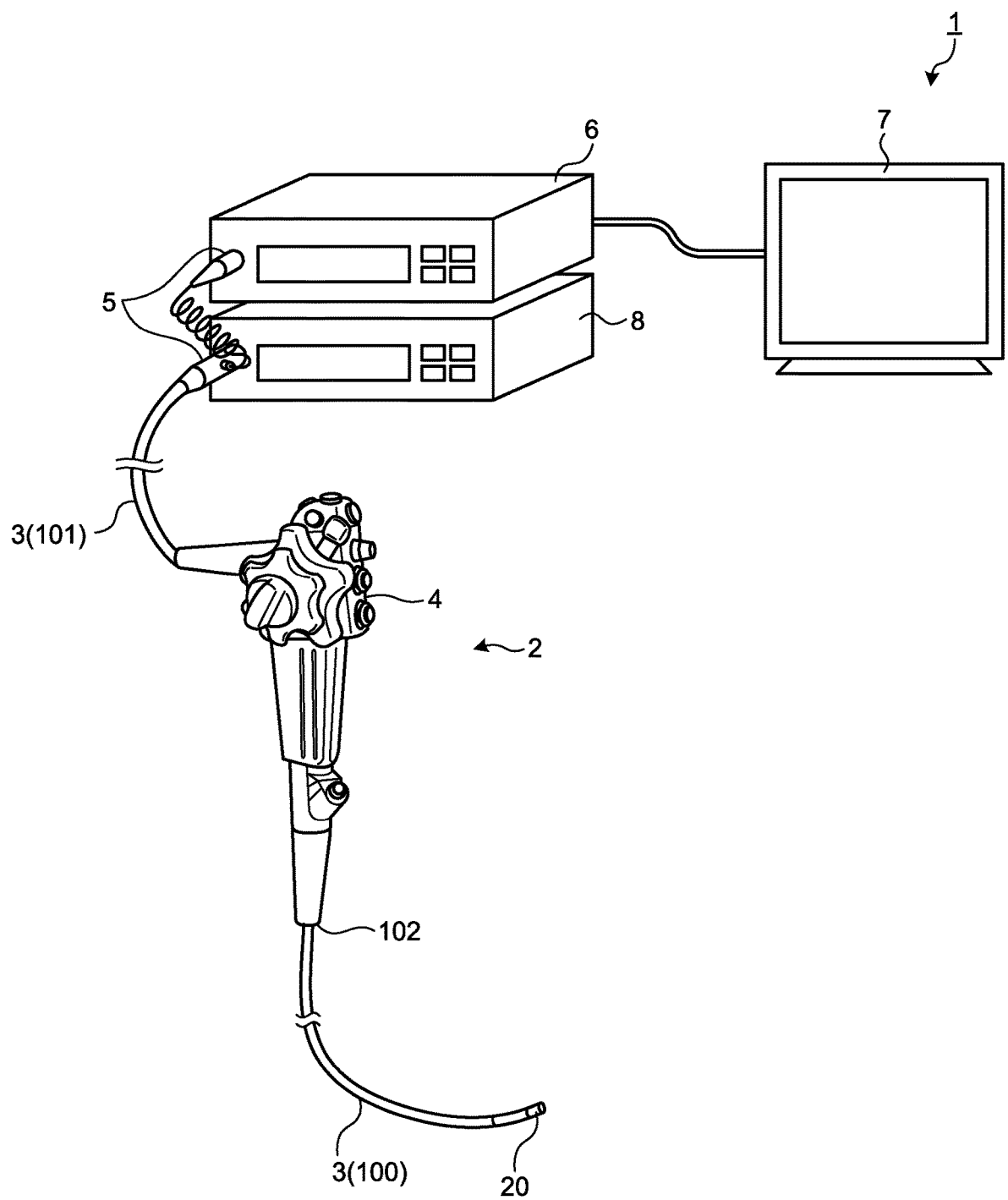
FIG. 1 is a schematic diagram schematically illustrating an entire configuration of an endoscope system according to a first embodiment of the disclosure.

FIG. 1 is a schematic diagram schematically illustrating the entire configuration of an endoscope system according to a first embodiment of the disclosure. An endoscope system 1 illustrated in FIG. 1 includes an endoscope 2, a control device 6 (processor), a display device 7, and a light source device 8.

The endoscope 2 includes a transmission cable 3, an operating unit 4, and a connector unit 5. The endoscope 2 generates an imaging signal by capturing an image of the inside of the body of the subject with an insertion portion 100, which is a part of the transmission cable 3, inserted into the body cavity of the subject, and outputs the imaging signal to the control device 6 via a universal cord 101, which is a part of the transmission cable 3. Furthermore, the endoscope 2 is provided with an imaging unit 21 on one end side of the transmission cable 3 and at a distal end portion 20 side of the insertion portion 100 to be inserted into the body cavity of the subject. The imaging unit 21 generates an imaging signal by capturing an image of the inside of the body cavity of the subject. To a proximal end 102 side of the insertion portion 100, an operating unit 4 that receives various operations on the endoscope 2 is connected. The imaging signal generated by the imaging unit 21 is output to the connector unit 5 via the universal cord 101, which is a part of the transmission cable 3 having a length of at least 10 cm. The connector unit 5 is detachably connected to the control device 6 and the light source device 8, performs predetermined signal processing on the imaging signal output by the imaging unit 21, and outputs the resultant signal to the control device 6.

The control device 6 performs predetermined image processing on the imaging signal input from the connector unit 5, outputs the resultant signal to the display device and controls the entire endoscope system 1 as a whole.

The display device 7 displays an image corresponding to the imaging signal input from the control device 6 under the control of the control device 6. The display device 7 is configured using an organic electroluminescence (EL) display, a liquid crystal display, or the like.

The light source device 8 is configured using, for example, a halogen lamp, a white light-emitting diode (LED), or the like, and emits illumination light toward the subject from the distal end portion 20 side of the insertion portion 100 of the endoscope 2 through the connector unit 5 and the transmission cable 3.

Functional Configuration of Main Part or Endoscope System

Figure 2:
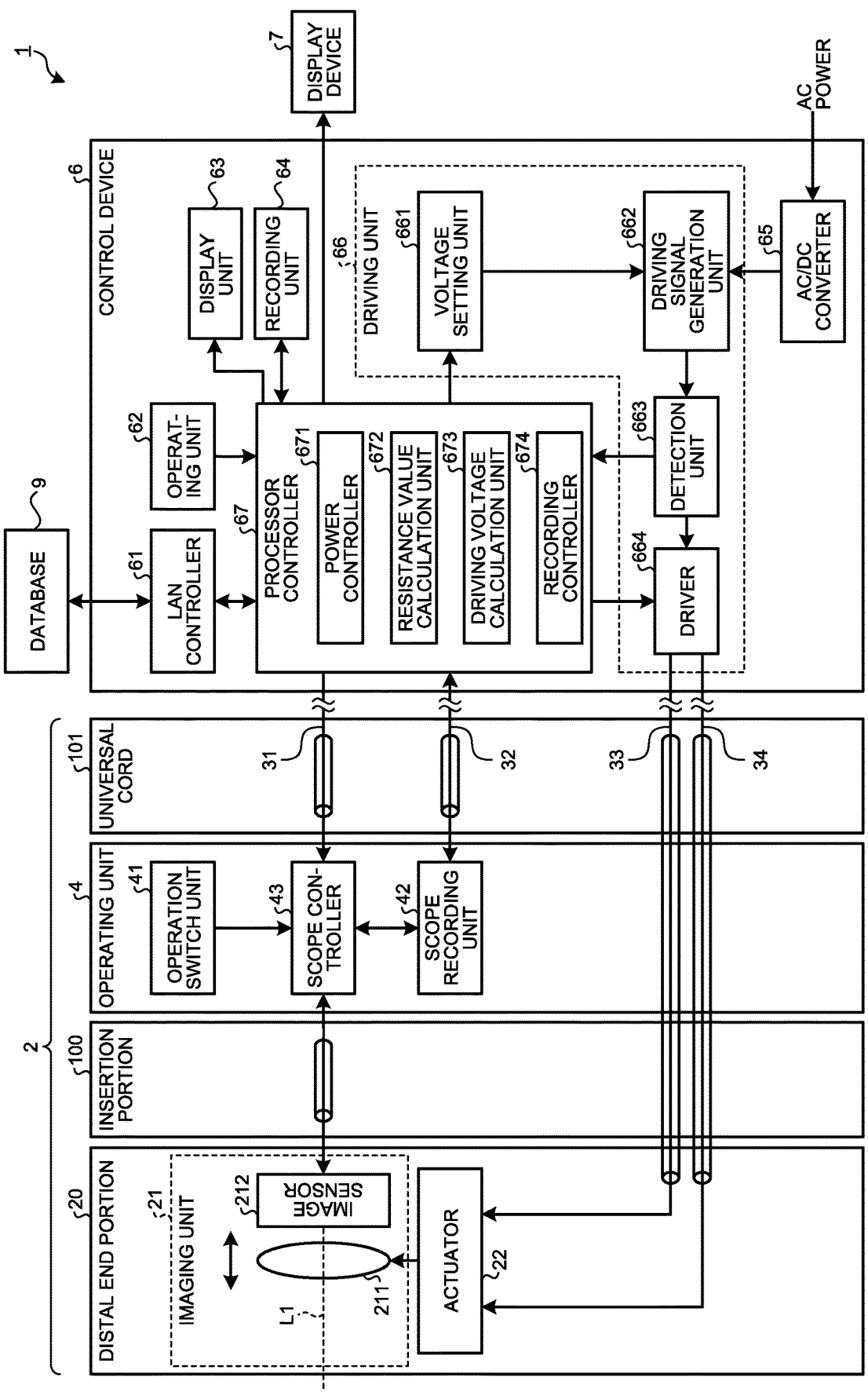
FIG. 2 is a block diagram illustrating a functional configuration of a main part of the endoscope system according to the first embodiment of the disclosure.

Next, a functional configuration of a main part of the above-described endoscope system 1 will be described. FIG. 2 is a block diagram illustrating a functional configuration of a main part of the endoscope system 1.

Configuration of Main Part of Endoscope

First, the distal end portion 20 and the operating unit 4 of the endoscope 2 will be described.

As illustrated in FIG. 2, the distal end portion. 20 includes the imaging unit 21 and an actuator 22.

The imaging unit 21 includes an optical system 211 and an image sensor 212.

The optical system 211 forms a subject image and is arranged so as to be movable along an optical axis L1 direction. The optical system 211 changes the focal length by being moved along the optical axis L1 direction by the actuator 22 described later. Specifically, the optical system 211 can form a subject image at two different focal lengths (telephoto side and wide angle side) by moving along the optical axis L1 direction. The optical system 211 is configured using one or a plurality of lenses and a holding frame that holds these lenses. The object driven by the actuator may be not only the optical system 211 itself, but also some optical elements included in the optical system 211. These optical elements may have not only a function for changing the focal length of the optical system 211, but also a function for changing the focal position (the position where focus is achieved) of the optical system 211.

The image sensor 212 generates image data by receiving the subject image formed by the optical system 211 and performing photoelectric conversion, and outputs the image data to the operating unit 4 described later. The image sensor 212 is configured using a charge coupled device (CCD), a complementary metal oxide semiconductor (CMOS), and other image sensors, an A/D conversion circuit, a P/S conversion circuit, an output amplifier, and the like.

The actuator 22 moves the optical system 211 to a predetermined position by moving the optical system 211 along the direction of the optical axis L1. The actuator 22 moves the optical system 211 to a predetermined position along the optical axis L1 by generating a magnetic field based on the electric power supplied from the control device 6. For example, when electric power is supplied from the control device 6, the actuator 22 generates a magnetic field to move the optical system 211 from the wide angle side to the telephoto side. The actuator 22 is configured using a voice coil motor, a stepping motor, or the like. Note that the actuator 22 may be constituted by an ultrasonic motor.

Next, the operating unit 4 will be described.

The operating unit 4 includes an operation switch unit 41, a scope recording unit 42, and a scope controller 43.

The operation switch unit 41 receives an input of instruction signals for various operations related to the endoscope 2. The operation switch unit 41 is configured using, for example, a button, a switch, a toggle switch, a log dial, and the like. Note that the operation switch unit 41 may be configured by a touch panel, a pressure sensor, or the like.

The scope recording unit 42 records various information and parameters related to the endoscope 2. Specifically, the scope recording unit 42 records an initial driving voltage for driving the actuator 22, an energizable time according to actuator drive required specifications, a rated current value of the actuator 22, identification information (scope ID) for identifying the endoscope 2, the driving voltage, driving voltage required specifications, and the like of the image sensor 212, and various programs executed by the endoscope 2. The scope recording unit 42 is configured using a nonvolatile memory such as an EEPROM or a Flash memory.

The scope controller 43 controls various operations related to the endoscope 2 under the control of the control device 6, performs predetermined signal processing on image data input from the image sensor 212, and outputs the resultant data to the control device 6. The scope controller 43 is configured using a field programmable gate array (FPGA), an application specific integrated circuit (ASIC), a microprocessor, and the like.

The transmission cable 3 includes a first signal line 31 for transmitting at least image data and a control parameter for controlling the scope controller 43, a second signal line 32 for acquiring or inputting various information recorded by the scope recording unit 42, and a third signal line 33 and a fourth signal line 34 for supplying electric power to the actuator 22.

Configuration of Main Part of Control Device

Next, a configuration of a main part the control device 6 will be described.

The control device 6 includes a LAN controller 61, an operating unit 62, a display unit 63, a recording unit (storage) 64, an AC/DC converter 65, a driving unit 66, and a processor controller 67.

The LAN controller 61 transmits or receives predetermined information by performing bidirectional communication with an external database 9 via a network under the control of the processor controller 67. The LAN controller 61 is configured using a communication module.

The operating unit 62 receives an input of instruction signals for various operations related to the endoscope system 1. The operating unit 62 is configured using, for example, a mouse, a keyboard, a button, a switch, a toggle switch, a jog dial, a touch panel, and the like.

The display unit 63 displays various information related to the endoscope system 1 under the control of the processor controller 67. The display unit 63 is configured using a display panel such as a liquid crystal display, an organic EL display, or the like.

The recording unit 64 records various information related to the control device 6, various programs executed by the control device 6, and image data. The recording unit 64 is configured using a volatile memory, a nonvolatile memory, a solid state drive (SSD), a hard disk drive (HDD), a memory card, and the like.

The AC/DC converter 65 converts AC power supplied from the outside of the control device 6 into DC power and outputs the DC power to the driving unit 66. The AC/DC converter 65 is configured using a transformer, a rectifier, a capacitor, and the like.

The driving unit 66 drives the actuator 22 by supplying electric power to the actuator 22 provided at the distal end portion 20 of the endoscope 2 under the control of the processor controller 67. The driving unit 66 includes a voltage setting unit 661, a driving signal generation unit 662, a detection unit 663, and a driver 664.

The voltage setting unit 661 sets the driving voltage output from the driving signal generation unit 662 under the control of the processor controller 67. The voltage setting unit 661 is configured using a D/A conversion circuit, a comparator circuit, and the like.

The driving signal generation unit 662 outputs a driving signal in which the voltage of the DC power supply input from the AC/DC converter 65 is adjusted to the driving voltage set by the voltage setting unit 661, to the driver 664. The driving signal generation unit 662 is configured using a regulator or the like.

The detection unit 663 is provided between the driver 664 and the driving signal generation unit 662, detects the magnitude of the driving signal supplied by the driving signal generation unit 662, and outputs the detection result to the processor controller 67. The detection unit 663 is configured using an ammeter, a wattmeter, an A/D conversion circuit, and the like. Specifically, the detection unit 663 is provided between the driver 664 and the driving signal generation unit 662, and measures electrical output characteristics of the driving signal generation unit 662. The characteristics include electric power (W=I·V), current (I), and voltage (V), and various power measurement ICs for measuring these characteristics are provided by semiconductor manufacturers. Some of these ICs can measure output electric power and output current, and others can measure output electric power, output current, and output voltage. The measured values from the ICs include those output as analog signals and those output as digital signals. For an IC that outputs a measured value as an analog signal, a digital value can be obtained by combining an AD conversion circuit. When it necessary to measure voltage in an IC that outputs only electric power and current, the voltage can be obtained by dividing the value of electric power from the IC by the value of current from the IC.

The driver 664 supplies electric power to the actuator 22 by outputting the driving voltage input from the driving signal generation unit 662 to the third signal line 33 and the fourth signal line 34 under the control of the processor controller 67. The driver 664 is configured using an H-bridge circuit or the like. Based on the control signal of the processor controller 67, the driver 664 can set the driving signal output from the driving signal generation unit 662 in a state of being transmitted to the transmission cable 3 and a state of being prohibited from being transmitted, and can also set the direction of application of the driving signal to the transmission cable 3.

The processor controller 67 performs overall control on the units included in the endoscope system 1. The processor controller 67 is configured using a central processing unit (CPU), an ASIC, an FPGA, or the like. The processor controller 67 includes a power controller 671, a resistance value calculation unit 672, a driving voltage calculation unit 673, and a recording controller 674.

The power controller 671 causes the driving signal generation unit 662 to supply a preset initial driving voltage value to the actuator 22 for a predetermined time.

The resistance value calculation unit 672 calculates a combined resistance value including the resistance value of the transmission cable 3 and the resistance value of the actuator 22, based on at least the magnitude of the driving signal detected by the detection unit 663. For example, the resistance value calculation unit 672 calculates a combined resistance value including the resistance value of the transmission cable 3 and the resistance value of the actuator 22, based on the initial driving voltage value and the current value detected by the detection unit 663. As the initial driving voltage value, data set in the voltage setting unit 661 can be used (indicating digital data set in the DA converter, which is a voltage parameter corresponding to the driving voltage). Alternatively, the driving voltage of the driving signal output from the driving signal generation unit 662 as a result of setting initial data in the voltage setting unit 661 can be used as the initial driving voltage value. The driving signal of the driving voltage generated by the driving signal generation unit 662 based on the voltage parameter is affected by an error in characteristics of a circuit included in the driving signal generation unit 662. Due to this effect, the driving voltage also causes an error. It is therefore desirable to directly measure the output (driving voltage) of the driving signal generation unit 662 in order to accurately obtain the initial driving voltage value. This voltage can be measured using the detection unit 663 as described above. In order to increase the measurement accuracy of this voltage, it is desirable to measure the output of the detection unit 663 with an AD converter having higher resolution than that of the DA converter in the voltage setting unit 661. More specifically, the resistance value calculation unit 672 calculates a combined resistance value including the resistance value of the transmission cable 3 and the resistance value of the actuator 22 using any one of the current value, the voltage value, and the power value of the driving signal.

Specifically, the resistance value calculation unit 672 calculates the combined resistance value according to the following patterns. The resistance value can be determined using any one of (1) the current value of the driving signal and the initial driving voltage value of the driving signal, (2) the power value of the driving signal and the initial driving voltage value of the driving signal, (3) the current value of the driving signal and the power value of the driving signal, (4) the current value of the driving signal and the voltage value of the driving signal, and (5) the power value of the driving signal and the voltage value of the driving signal. Preferably, the resistance value calculation unit 672 calculates a combined resistance value including the resistance value of the transmission cable 3 and the resistance value of the actuator 22 using the magnitudes of the driving signals of the patterns (3) to (5).

The driving voltage calculation unit 673 calculates the driving voltage of the actuator 22, based on the combined resistance value calculated by the resistance value calculation unit 672 and a preset rated current value of the actuator 22.

The recording controller 674 causes the scope recording unit 42 to record the driving voltage calculated by the driving voltage calculation unit 673.

Process of Endoscope System

Figure 3:
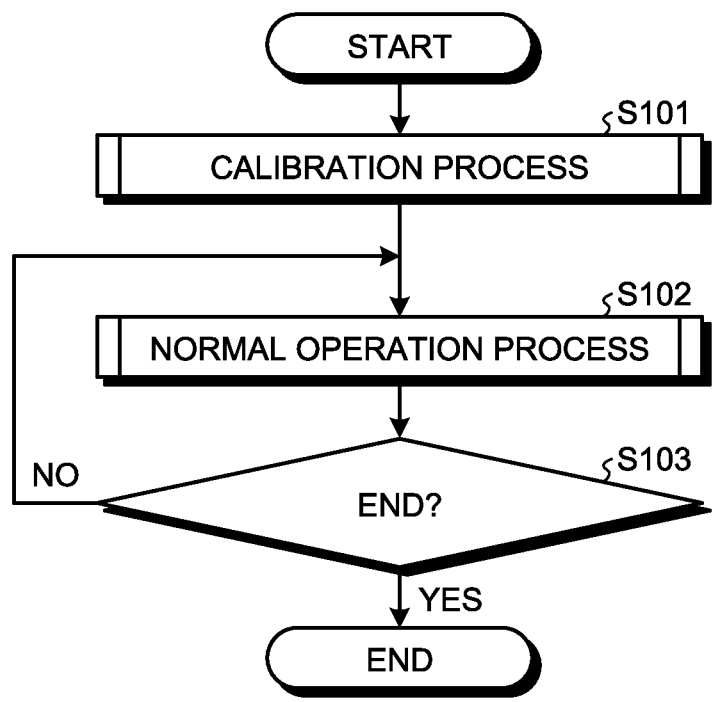
FIG. 3 is a flowchart illustrating an outline of a process executed by the endoscope system according to the first embodiment of the disclosure.

Next, the process executed by the endoscope system 1 will be described. The following describes the drive control of the actuator 22. FIG. 3 is a flowchart illustrating an outline of the process executed by the endoscope system 1.

As illustrated in FIG. 3, first, when activated, the endoscope system 1 executes a calibration process to adjust the driving voltage of the actuator 22 (Step S101). Details of the calibration process will be described later.

Subsequently, the endoscope system 1 executes a normal operation process of driving the actuator 22 in accordance with the operation on the operation switch unit 41 with the driving voltage adjusted through the above-described calibration process (Step S102). Details of the normal operation process will be described later.

After that, when an instruction signal for ending the examination is input according to the operation on the operation switch unit 41 or the operating unit 62 (Step S103: Yes), the endoscope system 1 ends the processing. On the other hand, when no instruction signal for ending the examination is input according to the operation on the operation switch unit 41 or the operating unit 62 (Step S103: No), the process executed by the endoscope system 1 returns to Step S102 described above.

Calibration Process

Figure 4:
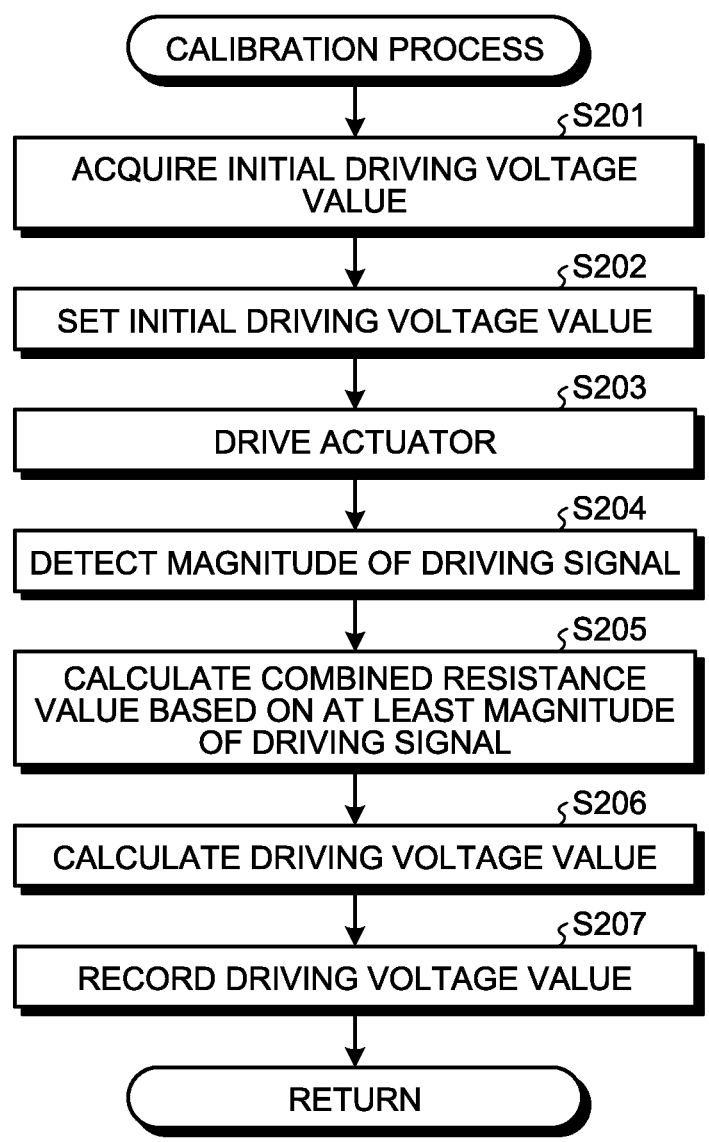
FIG. 4 is a flowchart illustrating an outline of a calibration process in FIG. 3.

Next, details of the calibration process described in Step S101 in FIG. 3 will be described. FIG. 4 is a flowchart illustrating an outline of the calibration process.

As illustrated in FIG. 4, first, the power controller 671 acquires the initial driving voltage value recorded in the scope recording unit 42 of the endoscope 2 connected to the control device 6 (Step S201), and causes the voltage setting unit 661 to set the driving voltage supplied by the driving signal generation unit 662 to the initial driving voltage value (Step S202).

Figure 5:
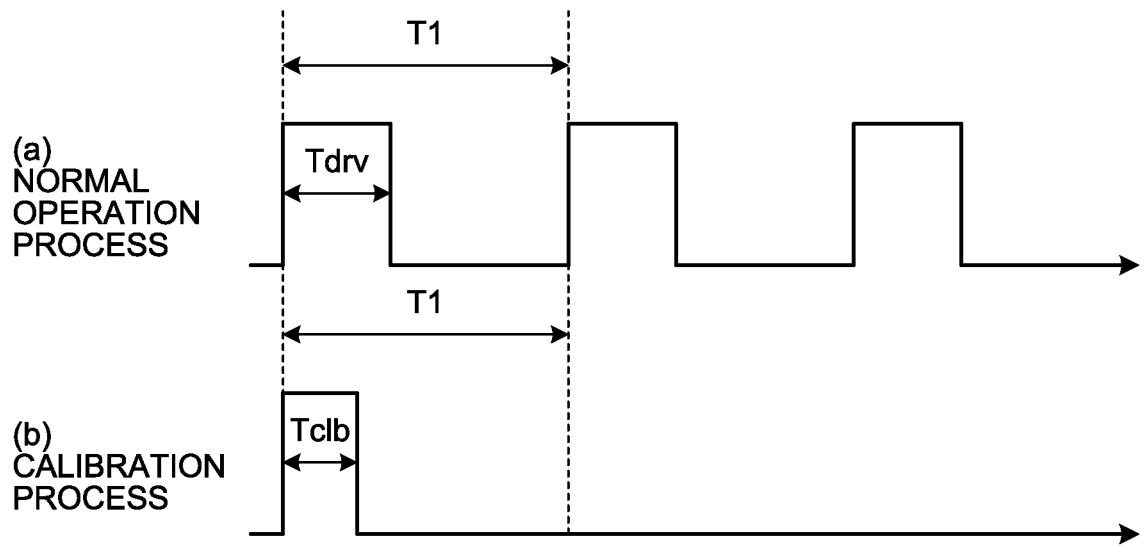
FIG. 5 is a time chart schematically explaining a situation where a power controller according to the first embodiment of the disclosure supplies a driver with a driving voltage in the calibration process.

Subsequently, the power controller 671 drives the actuator 22 by causing the driver 664 to supply driving power to the actuator 22 (Step S203). In this case, as illustrated in FIG. 5, the power controller 671 causes the driver 664 to energize the actuator 22 with the initial driving voltage for a second energizing time Tclb shorter than a first energizing time Tdrv. Here, the first energizing time Tdrv is an energizing time per unit time T1 when the driver 664 energizes the actuator 22 with electric power to adjust the position of the optical system 211 on the optical axis L1.

After that, the detection unit 663 detects the magnitude of the driving signal (Step S204). In this case, the detection unit 663 outputs the detection result to the processor controller 67.

Subsequently, the resistance value calculation unit 672 calculates a combined resistance value obtained by combining the resistance value of the actuator 22 and the resistance value of the transmission cable 3, based on at least the magnitude of the driving signal detected by the detection unit 663 (Step S205). As described above, the resistance value calculation unit 672 can use the data set in the voltage setting unit 661 or the driving voltage of the driving signal output from the driving signal generation unit 662, as the initial driving voltage value. More specifically, the resistance value calculation unit 672 calculates the combined resistance value using the above-described patterns (3) to (5).

After that, the driving voltage calculation unit 673 calculates a driving voltage value based on the combined resistance value calculated by the resistance value calculation unit 672 and the rated current value of the actuator 22 (Step S206).

Subsequently, the recording controller 674 records the driving voltage value calculated by the driving voltage calculation unit 673 in the scope recording unit 42 of the endoscope 2 connected to the control device 6 (Step S207). After Step S207, the endoscope system 1 returns to the main routine in FIG. 3.

Normal Operation Processing

Next, details of the normal operation process described in Step S102 in FIG. 3 will be described. FIG. is a flowchart illustrating an outline of the normal operation process.

Figure 6:
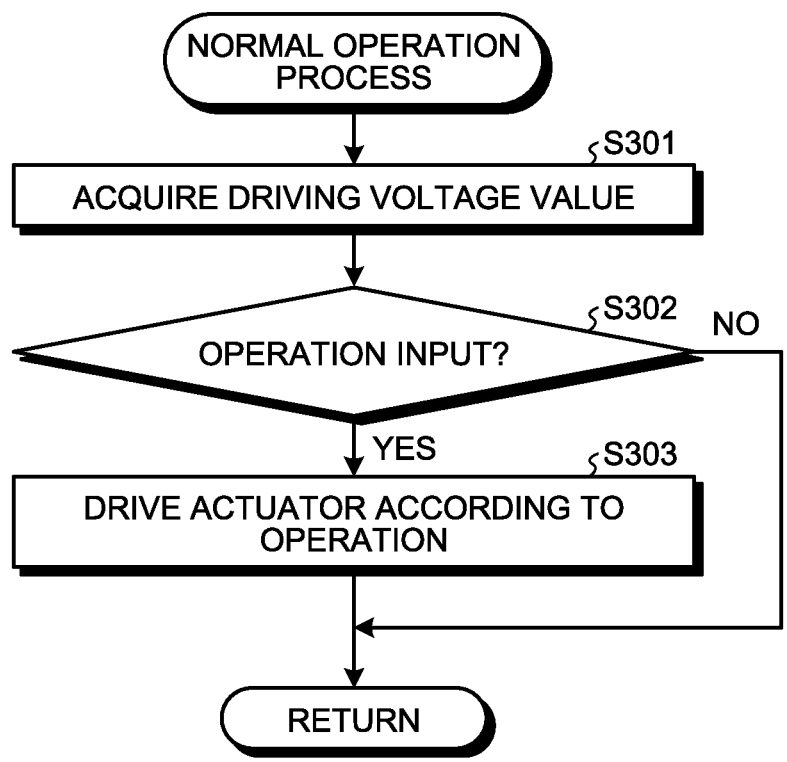
FIG. 6 is a flowchart illustrating an outline of a normal operation process in FIG. 3.

As illustrated in FIG. 6, first, the power controller 671 acquires the driving voltage value recorded in the scope recording unit 42 of the endoscope 2 connected to the control device 6 (Step S301). Specifically, the power controller 671 acquires the driving voltage value recorded in the scope recording unit 42 of the endoscope 2 connected to the control device 6, and sets the driving voltage value in the voltage setting unit 661. The driving voltage value is a voltage parameter set in the voltage setting unit 661, and an analog signal generated based on this parameter is input to the driving signal generation unit 662. The driving signal generation unit 662 generates a driving signal with the driving voltage for driving the actuator, based on the analog signal. With this operation, the actuator can be driven by the driving signal of the driving voltage determined through the calibration process.

Subsequently, when an instruction signal for moving the optical system. 211 along the optical axis L1 direction is input according to the operation on the operation switch unit 41 (Step S302: Yes), the power controller 671 causes the driver 664 to supply electric power to the actuator 22 according to the operation on the operation switch unit 41, thereby driving the actuator 22 (Step S303). After Step S303, the endoscope system 1 returns to the main routine in FIG. 3. On the other hand, when no instruction signal for moving the optical system 211 along the optical axis L1 direction is input according to the operation on the operation switch unit 41 (Step S302: No), the endoscope system 1 returns to the main routine in FIG.

According to the first embodiment of the disclosure described above, the driving voltage calculation unit 673 calculates the driving voltage of the actuator 22 based on the combined resistance value calculated by the resistance value calculation unit 672 and the preset rated current value of the actuator 22, and the recording controller 674 records the driving voltage calculated by the driving voltage calculation unit 673 in the scope recording unit 42, whereby the actuator 22 can be driven reliably.

Furthermore, according to the first embodiment of the disclosure, the power controller 671 causes the driver 664 to energize the actuator 22 with the initial driving voltage for the second energizing time Tclb shorter than the first energizing time Tdrv, which is an energizing time per unit time T1 when the driver 664 energizes the actuator 22 with electric power to adjust the position of the optical system 211 on the optical axis L1, whereby the calibration process can be performed reliably even with the actuator 22 that can be energized only for a short period of time.

According to the first embodiment of the disclosure, the driving voltage calculation unit 673 calculates the driving voltage of the actuator 22 based on the combined resistance value calculated by the resistance value calculation unit 672 and the preset rated current value of the actuator 22, whereby an accurate combined resistance value can be calculated through simple processing even when the cable length of the transmission cable 3 changes due to repair or the like.

Furthermore, according to the first embodiment of the disclosure, the driving voltage calculation unit 673 calculates the driving voltage of the actuator 22 based on the combined resistance value calculated by the resistance value calculation unit 672 and the preset rated current value of the actuator 22, whereby an accurate combined resistance value can be calculated even when the resistance value of the actuator 22 and the resistance value of the transmission cable 3 change due to aging deterioration, so that the accurate driving voltage of the actuator 22 can be calculated.

Furthermore, according to the first embodiment of the disclosure, since the calibration process is performed at the time of activation, a test of the subject can be started promptly.

While the recording controller 674 records the driving voltage calculated by the driving voltage calculation unit 673 in the scope recording unit 42 in the first embodiment of the disclosure, this should not be construed in a limiting sense. For example, the driving voltage may be recorded in the recording unit 64 in the control device 6 or may be recorded in the database 9 via the LAN controller 61. In this case, the scope ID of the endoscope connected to the control device 6, the rated current of the actuator 22, and the driving voltage may be associated with each other and recorded in the database 9 or the recording unit 64.

Second Embodiment

Next, a second embodiment of the disclosure will be described. An endoscope system according to the second embodiment has a different configuration and a different calibration process from the endoscope system 1 according to the above-described first embodiment. Specifically, while the driving voltage of the actuator 22 during the normal operation is calculated by single calculation of the combined resistance value in the above-described first embodiment, the driving voltage of the actuator during the normal operation is calculated while increasing the driving voltage step by step in the second embodiment. The following describes the configuration of the endoscope system according to the second embodiment, followed by a calibration process executed by the endoscope system according to the second embodiment. Note that the components that are the same as those in the endoscope system 1 according to the above-described first embodiment are denoted by the same reference numerals, and a detailed description thereof is omitted.

Functional configuration of main part of endoscope system

Figure 7:
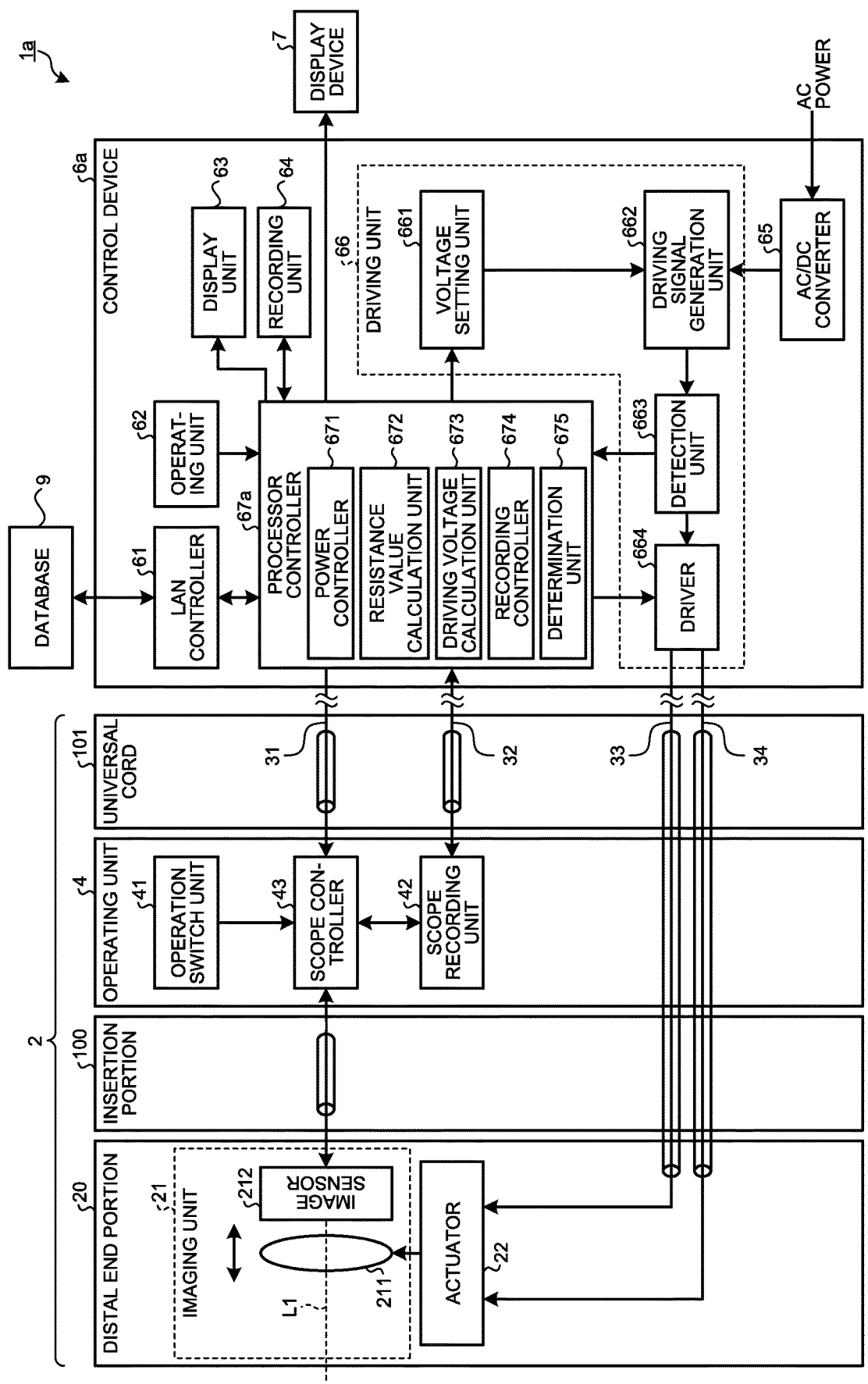
FIG. 7 is a block diagram illustrating a functional configuration of a main part of an endoscope system according to a second embodiment of the disclosure.

FIG. 7 is a block diagram illustrating a functional configuration of a main part of the endoscope system according to the second embodiment. An endoscope system 1*a* illustrated in FIG. 7 includes a control device 6*a* instead of the control device 6 of the endoscope system 1 according to the above-described first embodiment.

Configuration of Control Device

The control device 6*a* illustrated in FIG. 7 includes a processor controller 67*a* instead of the processor controller 67 according to the above-described first embodiment. Furthermore, the processor controller 67*a* includes a determination unit 675 in addition to the configuration of the processor controller 67 according to the above-described first embodiment.

The determination unit 675 determines whether the difference between the current value detected by the detection unit 663 and the preset rated current value of the actuator 22 is equal to or smaller than a predetermined value.

Calibration Process

Figure 8:
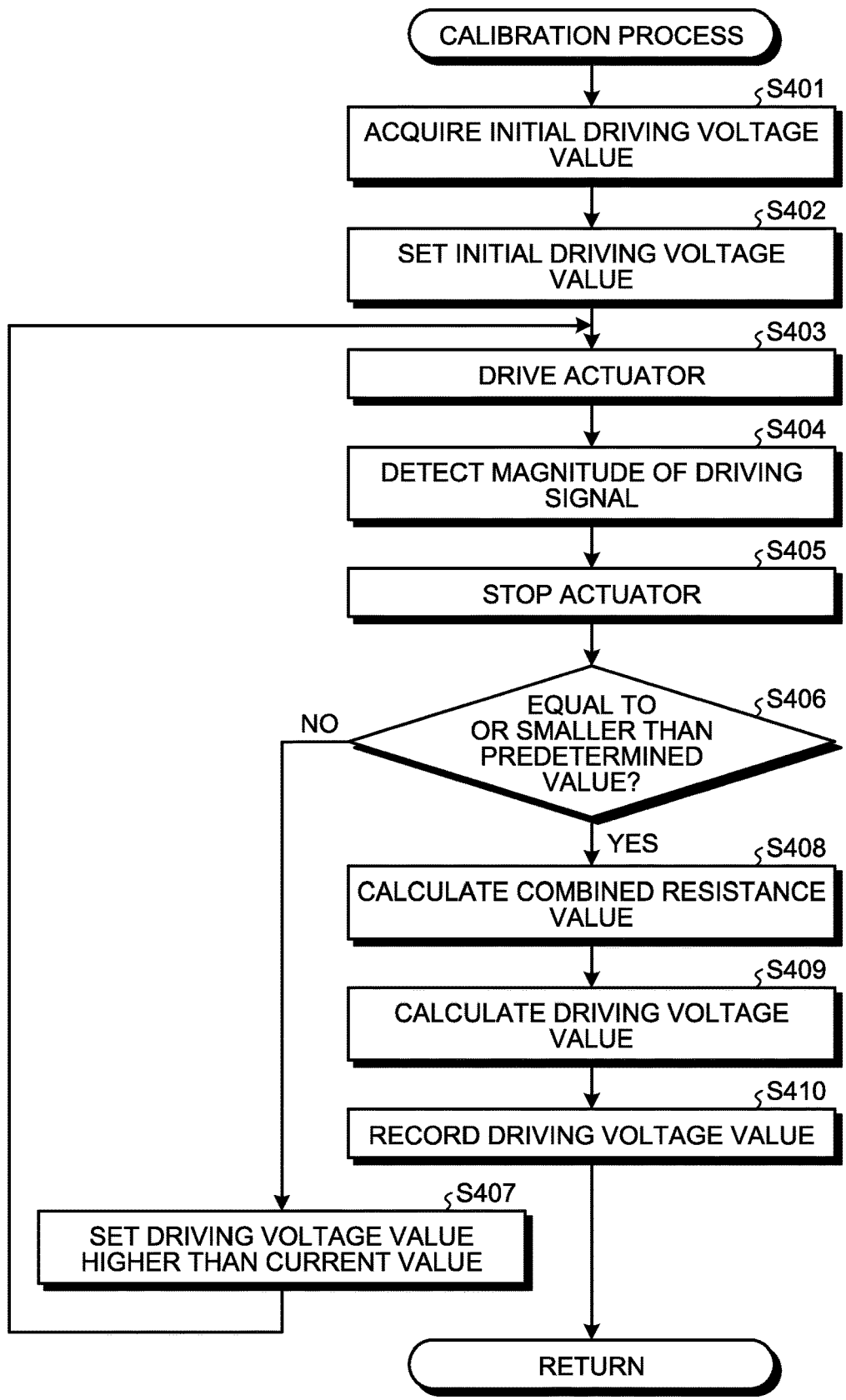
FIG. 8 is a flowchart illustrating an outline of calibration process executed by the endoscope system according to the second embodiment of the disclosure.

Next, a calibration process performed by the endoscope system 1*a* will be described FIG. 8 is a flowchart illustrating an outline of the calibration process executed by the endoscope system 1*a* according to the second embodiment. In FIG. 8, Steps S401 to S404 respectively correspond to Steps S201 to S204 in FIG. 4 described above.

In Step S405, the power controller 671 stops the actuator 22 by blocking the driving power supplied to the actuator 22 by the driver 664.

Subsequently, the determination unit 675 determines whether the difference between the magnitude of the driving signal detected by the detection unit 663 and the rated current value of the actuator 22 is equal to or smaller than a predetermined value (Step S406). If the determination unit 675 determines that the difference between the magnitude (current value) of the driving signal detected by the detection unit 663 and the rated current value of the actuator 22 is equal to or smaller than a predetermined value (Step S406: Yes), the process executed by the endoscope system 1*a* proceeds to Step S408 described below. On the other hand, if the determination unit 675 determines that the difference between the magnitude (current value) of the driving signal detected by the detection unit 663 and the rated current value of the actuator 22 is not equal to or smaller than a predetermined value (Step S406: No), the process executed by the endoscope system 1*a* proceeds to Step S407 described later.

Figure 9:
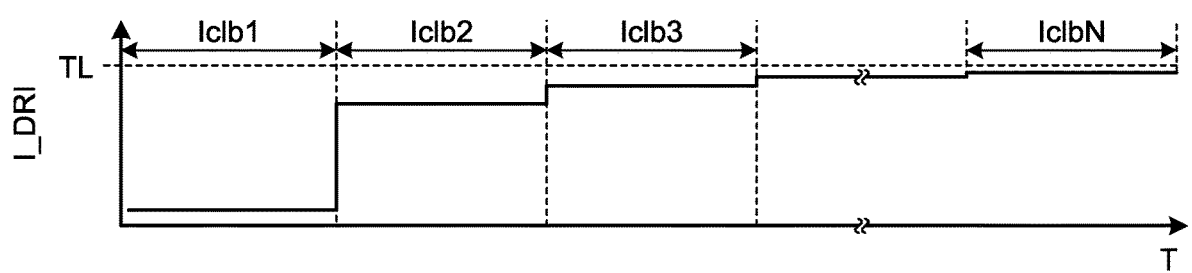
FIG. 9 is a time chart schematically explaining a situation where a power controller according to the second embodiment of the disclosure supplies a driver with a driving voltage in the calibration process.

In Step S407, the power controller 671 causes the voltage setting unit 661 to set the driving voltage value in the driving signal generation unit 662 higher than the current value. Specifically, the power controller 671 causes the voltage setting unit 661 to set the driving voltage value in the driving signal generation unit 662 so as to increase step by step such that the current value of the driving signal detected by the detection unit 663 gradually approaches a rated current value TL of the actuator 22. In this case, as illustrated in FIG. 9, when the driver 664 energizes the actuator 22 with electric power to adjust the position of the optical system 211 on the optical axis L1, the power controller 671 causes the driving signal generation unit 662 to supply the driving voltage value to the actuator 22 at predetermined time intervals while increasing the voltage value step by step from the initial driving voltage value (in the order from Iclb1 to Iclb2, Iclb3, Iclb4, ..., and IclbN (N=5 or more)). After Step S407, the process executed by the endoscope system 1a returns to Step S403.

In Step S408, the resistance value calculation unit 672 calculates a combined resistance value obtained by combining the resistance value of the actuator 22 and the resistance value of the transmission cable 3, based on the current driving voltage value supplied by the driving signal generation unit 662 and the magnitude of the driving signal detected by the detection unit 663. More specifically, the resistance value calculation unit 672 calculates the combined resistance value using the above-described patterns (3) to (5).

Subsequently, the driving voltage calculation unit 673 calculates the driving voltage value of the actuator 22 in the normal operation, based on the combined resistance value calculated by the resistance value calculation unit 672 and the magnitude of the driving signal detected by the detection unit 663 (Step S409). Specifically, the driving voltage calculation unit 673 calculates the driving voltage value of the actuator 22 in the normal operation, based on the combined resistance value calculated by the resistance value calculation unit 672 and the current value of the driving signal detected by the detection unit 663.

After that, the recording controller 674 records the driving voltage value calculated by the driving voltage calculation unit 673 in the scope recording unit 42 of the endoscope 2 connected to the control device 6 (Step S410). After Step S410, the process executed by the endoscope system 1a returns to the main routine in FIG. 3.

According to the second embodiment of the disclosure described above, the power controller 671 causes the voltage setting unit 661 to set the driving voltage value in the driving signal generation unit 662 so as to increase step by step such that the current value detected by the detection unit 663 gradually approaches the rated current value TL of the actuator 22, whereby the actuator 22 can be driven reliably even if the actuator 22 can be energized only for a short period of time.

Furthermore, while the power controller 671 causes the voltage setting unit 661 to set the driving voltage value in the driving signal generation unit 662 so as to increase step by step such that the current value detected by the detection unit 663 gradually approaches the rated current value IL of the actuator 22 in the second embodiment of the disclosure, this should not be construed in a limiting sense. The driving voltage value may be set to increase linearly so as to approach the rated current value TL. The driving voltage value may be set to increase so as to reach a value obtained by multiplying half of the difference between the magnitude (current value) of the driving signal detected by the detection unit 663 and the rated current value of the actuator 22 by a fixed value. The driving voltage value may be set to increase exponentially.

Third Embodiment

Next, a third embodiment of the disclosure will be described. An endoscope system according to the third embodiment has a different configuration and a different calibration process from the endoscope system 1 according to the above-described first embodiment. Specifically, in the third embodiment, the driving voltage vale when the difference between the magnitude (current value) of the driving signal detected by the detection unit and the rated current value of the actuator falls within a predetermined range is set as the driving voltage value of the actuator during the normal operation. The following describes the configuration of the endoscope system according to the third embodiment, followed by a calibration process executed by the endoscope system according to the third embodiment. Note that the components that are the same as those in the endoscope system 1 according to the above-described first embodiment are denoted by the same reference numerals, and a detailed description thereof is omitted.

Functional Configuration of Main Part of Endoscope System

Figure 10:
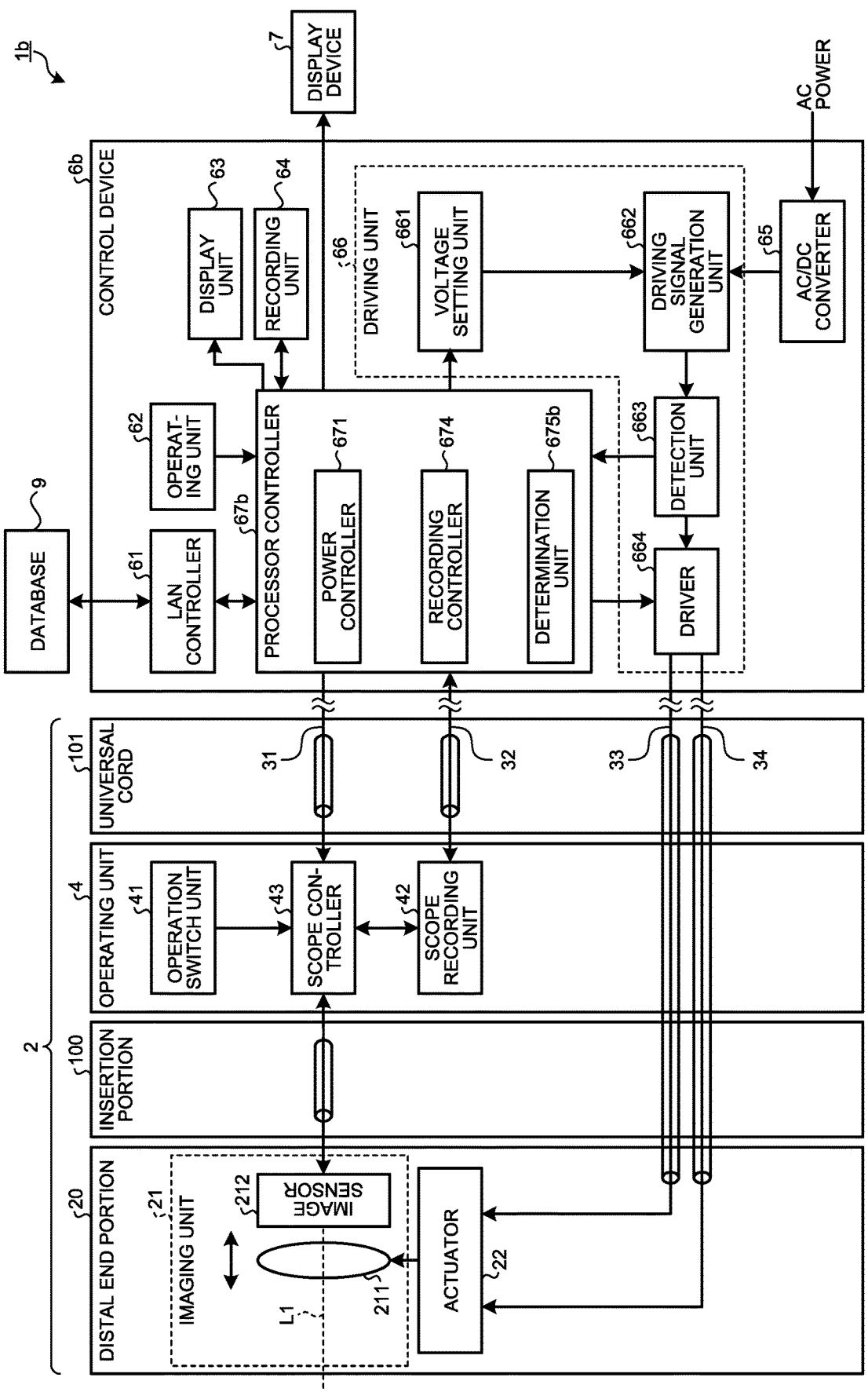
FIG. 10 is a block diagram illustrating a functional configuration of a main part of an endoscope system according to a third embodiment of the disclosure.

FIG. 10 is a block diagram illustrating a functional configuration of a main part of the endoscope system according to the third embodiment. An endoscope system 1b illustrated in FIG. 10 includes a control device 6b instead of the control device 6 of the endoscope system 1 according to the above-described first embodiment.

Configuration of Control Device

The control device 6b illustrated in FIG. 10 includes a processor controller 67b instead of the processor controller 67 according to the above-described first embodiment. Furthermore, the processor controller 67b includes a determination unit 675b in addition to the power controller 671 and the recording controller 674 according to the above-described first embodiment.

The determination unit 675b determines whether the difference between the magnitude of the driving signal detected by the detection unit 663 and the preset rated current value of the actuator 22 is equal to or smaller than a predetermined value. Specifically, the determination unit 675b determines whether the difference between the current value of the driving signal detected by the detection unit 663 and the preset rated current value of the actuator 22 is equal to or smaller than a predetermined value.

Calibration Process

Figure 11:
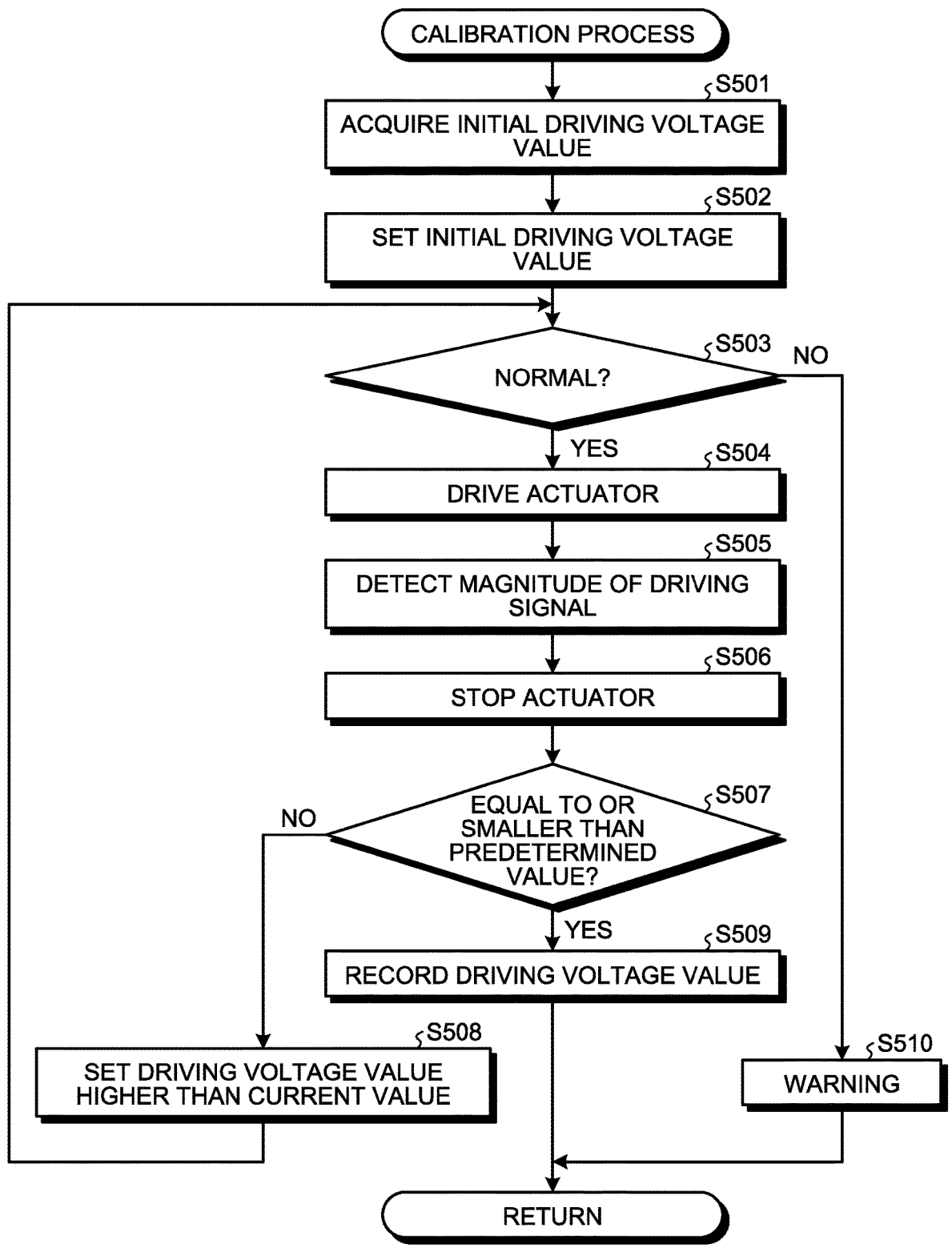
FIG. 11 is a flowchart illustrating an outline of a calibration process executed by the endoscope system according to the third embodiment of the disclosure.

FIG. 11 is a flowchart illustrating an outline of a calibration process executed by the endoscope system 1b. In FIG. 11, Steps S501 and S502 respectively correspond to Steps S201 and S202 in FIG. 4 described above.

In Step S503, if the actuator 22 is normal (Step S503: Yes), the process executed by the endoscope system 1b proceeds to Step S504 described later. On the other hand, if the actuator 22 is not normal (Step S503: No), the process executed by the endoscope system 1b proceeds to Step S510 described later.

Steps S504 and S505 respectively correspond to Steps S203 and S204 in FIG. 4 described above. After Step S505, the process executed by the endoscope system 1b proceeds to Step S506.

Subsequently, the power controller 671 stops the actuator 22 by stopping the driving power supplied to the actuator 22 by the driver 664 (Step S506).

Subsequently, the determination unit 675b determines whether the difference between the magnitude (current value) of the driving signal detected by the detection unit 663 and the rated current value of the actuator 22 is equal to or smaller than a predetermined value (Step S507). If the determination unit 675b determines that the difference between the magnitude (current value) of the driving signal detected by the detection unit 663 and the rated current value of the actuator 22 is equal to or smaller than a predetermined value (Step S507: Yes), the process executed by the endoscope system 1b proceeds to Step S509 described below. On the other hand, if the determination unit 675b determines that the difference between the magnitude (current value) of the driving signal detected by the detection unit 663 and the rated current value of the actuator 22 is not equal to or smaller than a predetermined value (Step S507: No), the process executed by the endoscope system 1b proceeds to Step S508 described later.

Figure 12:
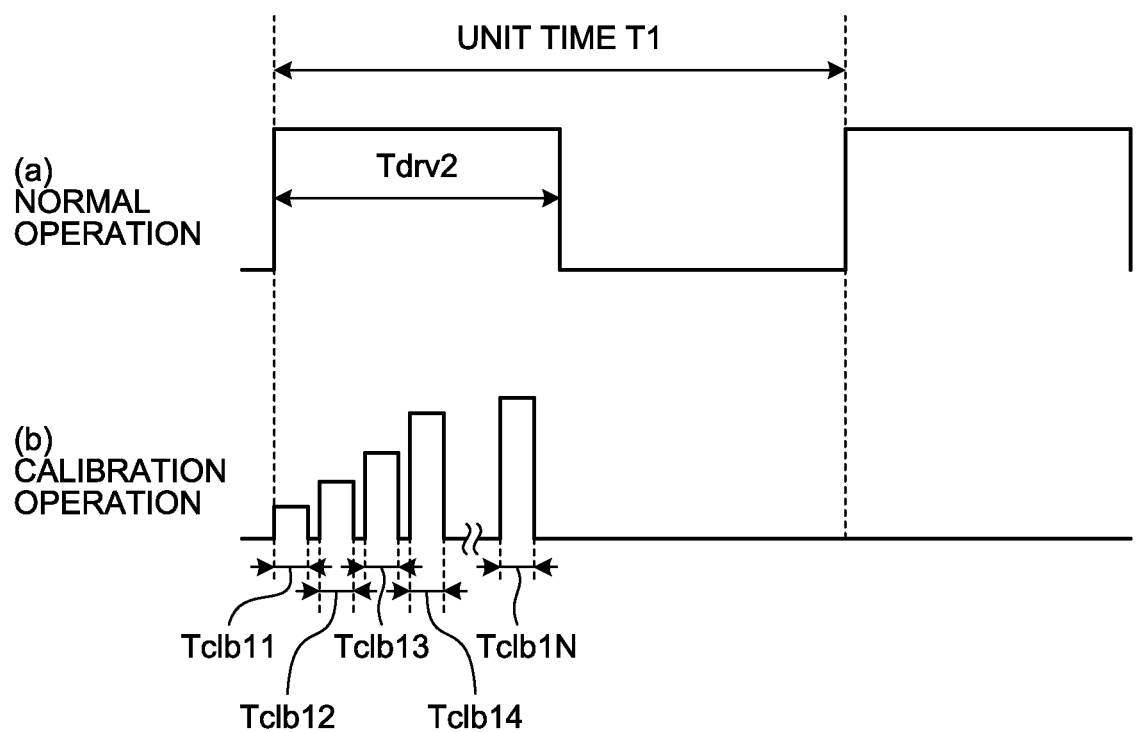
FIG. 12 is a time chart schematically explaining situation where a power controller according to the third embodiment of the disclosure supplies a driver with a driving voltage in the calibration process.

In Step S508, the power controller 671 causes the voltage setting unit 661 to set the driving voltage value in the driving signal generation unit 662 higher than the current value according to a predetermined condition. Specifically, as illustrated in FIG. 12, the power controller 671 causes the voltage setting unit 661 to set the driving voltage value in the driving signal generation unit 662 so as to increase step by step such that the current value detected by the detection unit 663 gradually approaches the rated current value TL1 of the actuator 22. Specifically, the power controller 671 causes setting such that the sum of energy (Tclb11+Tclb12+Tclb13+Tclb14+ . . . +Tclb1N (N=5 or more)) when the driving signal generation unit 662 supplies the driving voltage to the actuator 22 every time the voltage value is changed is kept below a first energy amount Tdrv2. The first energy amount Tdrv2 is the sum of energy per unit time T1 when the driver 664 energizes the actuator 22 with electric power to adjust the position of the optical system 211 on the optical axis L1. After Step S508, the process executed by the endoscope system 1b returns to Step S503.

In Step S509, the recording controller 674 records the driving voltage value set in the driving signal generation unit 662 by the voltage setting unit 661 in the scope recording unit 42 of the endoscope 2 connected to the control device 6. After Step S509, the process executed the endoscope system 1b returns to the main routine in FIG.

In Step S510, the processor controller 67b causes the display unit 63 or the display device 7 to display a warning indicating that the actuator 22 is abnormal. After S510, the process executed by the endoscope system 1b returns to the main routine in FIG. 3.

According to the third embodiment of the disclosure described above, the power controller 671 causes setting such that the sum of energy (Tclb11+Tclb12+Tclb13+Tclb14+ . . . +Tclb1N (N=5 or more)) when the driving signal generation unit 662 supplies the driving voltage to the actuator 22 every time the voltage value is changed is kept below a first energy amount Tdrv2. The first energy amount Tdrv2 is the sum of energy per unit time T1 when the driver 664 energizes the actuator 22 with electric power to adjust the position of the optical system 211 on the optical axis L1. Thus, the actuator 22 can be driven reliably.

Other Embodiments

Various types of embodiments can be formed by combining a plurality of components disclosed in the first to the third embodiments of the disclosure described above as appropriate. For example, some components may be deleted from all the components described in the first to the third embodiments of the disclosure described above. Furthermore, the components described in the first to the third embodiments of the disclosure described above may be combined as appropriate.

The control device and the light source device are separate components in the first to the third embodiments of the disclosure, but they may be formed integrally.

While the control device is provided with the processor controller and the driving unit 66 in the first to third embodiments of the disclosure, this should not be construed in a limiting sense. For example, the processor controller and the driving unit may be provided to a connector unit or an operating unit of an endoscope.

While the control device is provided with the processor controller and the driving unit in the first to third embodiments of the disclosure, this should not be construed in a limiting sense. The processor controller and the driving unit may be provided to an intermediate member connecting an endoscope with a control device. In other words, a dedicated intermediate unit for driving the actuator may be separately provided.

While the calibration process is performed at the time of activating the endoscope system in the first to the third embodiments of the disclosure, this should not be construed in a limiting sense. For example, the above-described calibration process may be performed at the time of pre-capture when the endoscope captures an image of image data. Of course, the calibration process may be performed according to the operation on the operating unit in other states such as sleep mode, or the calibration process may be performed before the start of a test of the subject.

Furthermore, while the energizing time for the actuator is controlled by controlling the driver in the first to the third embodiments of the disclosure, this should not be construed in a limiting sense. For example, the energizing time for the actuator may be controlled using a power shutdown unit, a switch, or the like.

Furthermore, wile the embodiments of the disclosure employ an endoscope system, for example, a capsule endoscope, a video microscope for capturing an image of a subject, a mobile phone having an imaging function, and a tablet terminal having an imaging function are also applicable.

Furthermore, while the first to the third embodiments of the disclosure employ an endoscope system including a flexible endoscope, an endoscope system including a rigid endoscope and an endoscope system including an industrial endoscope are also applicable.

While the first to the third embodiments of the disclosure employ an endoscope system including an endoscope to be inserted into the subject, for example, an endoscope system including a rigid endoscope and other endoscope systems such as a nasal sinus endoscope, an electrical scalpel, and inspection probe are also applicable.

In the first to the third embodiments of the disclosure, the "unit" described above can be read as "means", "circuit", or the like. For example, the control unit can be read as control means or a control circuit.

A program to be executed in the first to the third embodiments of the disclosure is file data in an installable format or an executable format, and is provided by being recorded on a computer-readable recording medium such as a CD-ROM, a flexible disk (FD), a CD-R, a digital versatile disk (DVD), a USB medium, or a flash memory.

Furthermore, the program to be executed in the first to the third embodiments of the disclosure may be configured to be provided by being stored on a computer connected to a network such as the Internet and downloaded via the network. Furthermore, the program to be executed in the first to the third embodiments of the disclosure may be provided or distributed via a network such as the Internet.

Furthermore, while signals are transmitted from the endoscope to the control device through the transmission cable in the first to the third embodiments of the disclosure, this is not necessarily wired communication and may be wireless communication. In this case, image signals or the like are transmitted from the endoscope to the control device according to a predetermined wireless communication standard (for example, Wi-Fi (registered trademark) or Bluetooth (registered trademark)). Of course, wireless communication may be performed according to any other wireless communication standards.

In the description of the flowcharts in the present specification, the context of processes between steps is clearly indicated using expressions such as "first", "after that", "subsequently", etc. However, the order of processes required for implementing the disclosure is not uniquely determined by their expressions. That is, the order of processes in the flowcharts described in this specification can be changed within a consistent range. Furthermore, the disclosure is not limited to such a program including a simple branching process, and a larger number of items may be comprehensively determined to be branched. In this case, a technique of artificial intelligence such as machine learning in prompting the user to perform manual operation and repeating learning may be used together. Furthermore, operation patterns performed by many experts may be learned, and deep learning may be performed by incorporating more complicated conditions.

According to the disclosure, there is an effect that an actuator can be driven reliably.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
one or a plurality of lenses configured to form a subject image;
an actuator configured to move the one or the plurality of lenses along an optical axis direction;
a driving signal generator configured to generate and supply a driving signal for driving the actuator;
a transmission cable electrically connecting the actuator and the driving signal generator, the transmission cable being configured to transmit the driving signal;
a detector configured to detect magnitude of the driving signal that is output from the driving signal generator to be supplied to the actuator through the transmission cable; and
a processor comprising hardware, the processor being configured to:
supply the driving signal with an initial driving voltage value to the actuator for a predetermined time;
calculate a combined resistance value including a resistance value of the transmission cable and a resistance value of the actuator, based on at least the detected magnitude of the driving signal;
calculate a driving voltage of the actuator, based on the calculated combined resistance value and a preset rated current value of the actuator; and
cause a storage to record the calculated driving voltage.

2. The endoscope system according to claim 1, wherein the processor is configured to cause the driving signal generator to supply the driving signal with the initial driving voltage value to the actuator for a second energizing time shorter than a first energizing time, the first energizing time being an energizing time per unit time when the driving signal generator supplies the driving signal to the actuator to adjust a position of the one or the plurality of lenses on the optical axis.

3. The endoscope system according to claim 1, wherein the processor is further configured to:
supply the driving signal to the actuator at predetermined time intervals while increasing a voltage value step by step from the initial driving voltage value;
determine whether a difference between the detected magnitude of the driving signal and the preset rated current value of the actuator is equal to or smaller than a predetermined value; and
calculate the combined resistance value based on at least the latest magnitude of the driving signal detected by the detector when it is determined that the difference is equal to or smaller than the predetermined value.

4. The endoscope system according to claim 1, wherein the detector is configured to detect an electrical output characteristic of at least one of electric power, current, and voltage of the driving signal as the magnitude of the driving signal.

5. The endoscope system according to claim 1, wherein the processor is further configured to supply the initial driving voltage value to the actuator when the endoscope system is activated.

6. The endoscope system according to claim 1, wherein:
the processor is further configured to execute a calibration process and a normal operation process;
the calibration process comprises:
supplying the driving signal to the actuator for the predetermined time;
calculating the combined resistance value;
calculating the driving voltage of the actuator; and
causing the storage to record the calculated driving voltage; and
the normal operation process comprises driving the actuator with the driving voltage recorded in the storage in the calibration process.

7. An endoscope system comprising:
one or a plurality of lenses configured to form a subject image;
an actuator configured to move the one or the plurality of lenses along an optical axis direction;
a driving signal generator configured to generate and supply a driving signal for driving the actuator;
a transmission cable electrically connecting the actuator and the driving signal generator, the transmission cable being configured to transmit the driving signal;
a detector configured to detect magnitude of the driving signal that is output from the driving signal generator to be supplied to the actuator through the transmission cable; and
a processor comprising hardware, the processor being configured to:
supply the driving signal to the actuator while changing a voltage value from an initial driving voltage value;
determine whether a difference between the detected magnitude of the driving signal and a preset rated current value of the actuator is equal to or smaller than a predetermined value; and
cause a storage to record the latest driving voltage of the driving signal supplied by the driving signal generator when it is determined that the difference is equal to or smaller than the predetermined value.

8. The endoscope system according to claim 7, wherein the processor is further configured to cause the driving signal generator to supply the driving signal at a second energy amount equal to or smaller than a first energy amount, the first energy amount being a sum of energy per unit time when the driving signal generator supplies the driving signal to the actuator to adjust a position of the one or the plurality of lenses on the optical axis, the second energy amount being a sum of energy when the driving signal generator supplies the driving signal to the actuator every time a voltage value is changed.

9. A control device being connectable with an endoscope, wherein the endoscope comprises:
one or a plurality of lenses configured to form a subject image; and
an actuator configured to move the one or the plurality of lenses along an optical axis direction, and
wherein the control device comprises:
a driving signal generator configured to generate and supply a driving signal for driving the actuator;
a transmission cable electrically connecting the actuator and the driving signal generator, the transmission cable being configured to transmit the driving signal;
a detector configured to detect magnitude of the driving signal that is output from the driving signal generator to be supplied to the actuator through the transmission cable; and
a processor comprising hardware, the processor being configured to:
supply the driving signal with an initial driving voltage value to the actuator for a predetermined time;
calculate a combined resistance value including a resistance value of the transmission cable and a resistance value of the actuator, based on at least the detected magnitude of the driving signal;
calculate a driving voltage of the actuator, based on the calculated combined resistance value and a preset rated current value of the actuator; and
cause a storage to record the calculated driving voltage.

10. A control device being connectable with an endoscope,
wherein the endoscope comprises:
one or a plurality of lenses configured to form a subject image; and
an actuator configured to move the one or the plurality of lenses along an optical axis direction, and
wherein the control device comprises:
a driving signal generator configured to generate and supply a driving signal for driving the actuator;
a transmission cable electrically connecting the actuator and the driving signal generator, the transmission cable being configured to transmit the driving signal;
a detector configured to detect magnitude of the driving signal that is output from the driving signal generator to be supplied to the actuator through the transmission cable; and
a processor comprising hardware, the processor being configured to:
supply the driving signal to the actuator while changing a voltage value from an initial driving voltage value;
determine whether a difference between the detected magnitude of the driving signal and a preset rated current value of the actuator is equal to or smaller than a predetermined value; and
cause a storage to record the latest driving voltage of the driving signal supplied by the driving signal generator when it is determined that the difference is equal to or smaller than the predetermined value.

11. A control method executed by an endoscope system that comprises: one or a plurality of lenses configured to form a subject image; an actuator configured to move the one or the plurality of lenses along an optical axis direction; a driving signal generator configured to generate and supply a driving signal for driving the actuator; and a transmission cable electrically connecting the actuator and the driving signal generator, the transmission cable being configured to transmit the driving signal, the control method comprising:
detecting magnitude of the driving signal that is output from the driving signal generator to be supplied to the actuator through the transmission cable;
supplying the driving signal with an initial driving voltage value to the actuator for a predetermined time;
calculating a combined resistance value including a resistance value of the transmission cable and a resistance value of the actuator, based on at least the detected magnitude of the driving signal;
calculating a driving voltage of the actuator, based on the calculated combined resistance value and a preset rated current value of the actuator; and
causing a storage to record the calculated driving voltage.

12. A control method executed by an endoscope system that comprises: one or a plurality of lenses configured to form a subject image; an actuator configured to move the one or the plurality of lenses along an optical axis direction; a driving signal generator configured to generate and supply a driving signal for driving the actuator; and a transmission cable electrically connecting the actuator and the driving signal generator, the transmission cable being configured to transmit the driving signal, the control method comprising:
detecting magnitude of the driving signal that is output from the driving signal generator to be supplied to the actuator through the transmission cable;
supplying the driving signal to the actuator while changing a voltage value from an initial driving voltage value;
determining whether a difference between the detected magnitude of the driving signal and a preset rated current value of the actuator is equal to or smaller than a predetermined value; and
causing a storage to record the latest driving voltage of the driving signal supplied by the driving signal generator when it is determined that the difference is equal to or smaller than the predetermined value.

13. A non-transitory computer-readable recording medium storing an endoscope image processing program to be executed by a computer, the program causing an endoscope system that comprises: one or a plurality of lenses configured to form a subject image; an actuator configured to move the one or the plurality of lenses along an optical axis direction; a driving signal generator configured to generate and supply a driving signal for driving the actuator; and a transmission cable electrically connecting the actuator and the driving signal generator, the transmission cable being configured to transmit the driving signal, to execute:
detecting magnitude of the driving signal that is output from the driving signal generator to be supplied to the actuator through the transmission cable;
supplying the driving signal with an initial driving voltage value to the actuator for a predetermined time;
calculating a combined resistance value including a resistance value of the transmission cable and a resistance value of the actuator, based on at least the detected magnitude of the driving signal;

calculating a driving voltage of the actuator, based on the calculated combined resistance value and a preset rated current value of the actuator; and causing a storage to record the calculated driving voltage.

14. A non-transitory computer-readable recording medium storing an endoscope image processing program to be executed by a computer, the program causing an endoscope system that comprises: one or a plurality of lenses configured to form a subject image; an actuator configured to move the one or the plurality of lenses along an optical axis direction; a driving signal generator configured to generate and supply a driving signal for driving the actuator; and a transmission cable electrically connecting the actuator and the driving signal generator, the transmission cable being configured to transmit the driving signal, to execute:

detecting magnitude of the driving signal that is output from the driving signal generator to be supplied to the actuator through the transmission cable;

supplying the driving signal to the actuator while changing a voltage value from an initial driving voltage value;

determining whether a difference between the detected magnitude of the driving signal and a preset rated current value of the actuator is equal to or smaller than a predetermined value; and causing a storage to record the latest driving voltage of the driving signal supplied by the driving signal generator when it is determined that the difference is equal to or smaller than the predetermined value.

* * * * *